United States Patent [19]

Sakurai et al.

[11] Patent Number: 4,989,023
[45] Date of Patent: Jan. 29, 1991

[54] STEREO TYPE EYE FUNDUS CAMERA

[75] Inventors: Aki Sakurai; Ryoichi Nadachi, both of Tokyo, Japan

[73] Assignee: Kabushiki Kaisha Topcon, Tokyo, Japan

[21] Appl. No.: 507,844

[22] Filed: Apr. 12, 1990

[30] Foreign Application Priority Data

Apr. 14, 1989 [JP] Japan .................................. 1-94753

[51] Int. Cl.5 ............................................ G03B 29/00
[52] U.S. Cl. ...................................... 354/62; 354/112
[58] Field of Search .................................. 354/62, 112

[56] References Cited

U.S. PATENT DOCUMENTS 4,469,416  9/1984  Isono ................................ 354/62 X Primary Examiner—Michael L. Gellner
Attorney, Agent, or Firm—Finnegan, Henderson, Farabow, Garrett & Dunner

[57] ABSTRACT

A stereo type eye fundus camera has an illumination optical system for illuminating the fundus of an eye to be tested, and a stereo type image formation optical system for simultaneously forming an image of the eye fundus on a sheet of film based on a reflected light from the eye fundus. The stereo type eye fundus camera also has a density pattern member for forming a density pattern image on the eye fundus.

12 Claims, 3 Drawing Sheets

FIG. I

STEREO TYPE EYE FUNDUS CAMERA

BACKGROUND OF THE INVENTION

1. Field of the Invention

This invention relates to a stereo eye fundus camera or an eye fundus camera for illuminating the fundus of an eye to be tested through an objective lens and guiding a reflected beam of light from the eye fundus to a stereo type image formation optical system in order to stereoscopically observe the eye fundus.

2. Description of the Prior Art

Heretofore, a stereo type eye fundus camera has an illumination optical system for illuminating the eye fundus through an objective lens. The illumination light is reflected by the eye fundus. A reflected beam of light from the eye fundus is split by a two-aperture diaphragm. The reflected beam which was split by the two-aperture diaphragm, is guided to a stereo type image formation optical system. And a man can stereoscopically observe the eye fundus by the stereo type image formation optical system.

Also, such split reflected beams are simultaneously separately imaged on respective portions of a sheet of film by the stereo type image formation optical system. By this, a pair of eye fundus images having a parallax are taken on a sheet of photograph.

Analysis of a three-dimensional configuration of the eye fundus is performed by comparing the pair of eye fundus images taken on the sheet of photograph. That is, various component parts of one fundus image are compared with the corresponding component parts of the other eye fundus image. And parallax is measured for each component part. By this, the three-dimensional configuration of the eye fundus is analyzed.

However, there are parts having uniform reflection factors in the eye fundus. There is also a part, like a papilla, having a high reflection factor in the eye fundus.

In such a case like this, when the eye fundus is taken using the conventional stereo type eye fundus camera, the eye fundus is taken as a plane image having a vague border even if there are irregularities on the eye fundus because the portion having uniform reflection factors is low in contrast. Therefore, it is difficult to compare the various component parts of a portion having the uniform reflection factors of one eye fundus image with the corresponding component parts of a portion having the uniform reflection factors of the other eye fundus image, and it is very difficult to three-dimensionally analyze the configuration of the eye fundus.

On the other hand, the papilla portion has a high reflection factor. Therefore, when the papilla is taken, it becomes overexposure. As a consequence, the analysis of the three-dimensional configuration of the papilla portion is difficult.

SUMMARY OF THE INVENTION

The object of the present invention is to provide a stereo type eye fundus camera capable of taking a photo of the eye fundus, in which analysis of a three-dimensional configuration of the eye fundus can be performed with ease even at portions having uniform reflection factors and at a papilla portion having a high refleciton factor.

In order to achieve the above object, according to the present invention, there is provided a stereo type eye fundus camera including an illumination optical system for illuminating the fundus of an eye to be tested, and a stereo type image formation optical system for simultaneously forming an image of the eye fundus on a sheet of film based on a reflected light from the eye fundus, said stereo type eye fundus camera further including a density pattern member adapted to form a density pattern image on said eye fundus.

According to this invention, a density pattern image is formed on the eye fundus by the density pattern member. That is, a shadow pattern as a density pattern image is formed on various component parts of the eye fundus (portions having uniform reflection factors, a papilla portion having a high reflection factor, etc.). When there are irregularities on the portions having uniform reflection factors, the papilla portion having a high reflection factor, the density pattern image changes in correspondence with the irregularities. Therefore, when a man looks the eye fundus through the stereo type image formation optical system, the eye fundus can be three-dimensionally observed. Similarly, analysis of the three-dimensional configuration is performed by comparing a density pattern image corresponding to one eye fundus image with a density pattern image corresponding to the other eye fundus image.

DETAILED DESCRIPTION OF THE EMBODIMENTS

Figure 1:
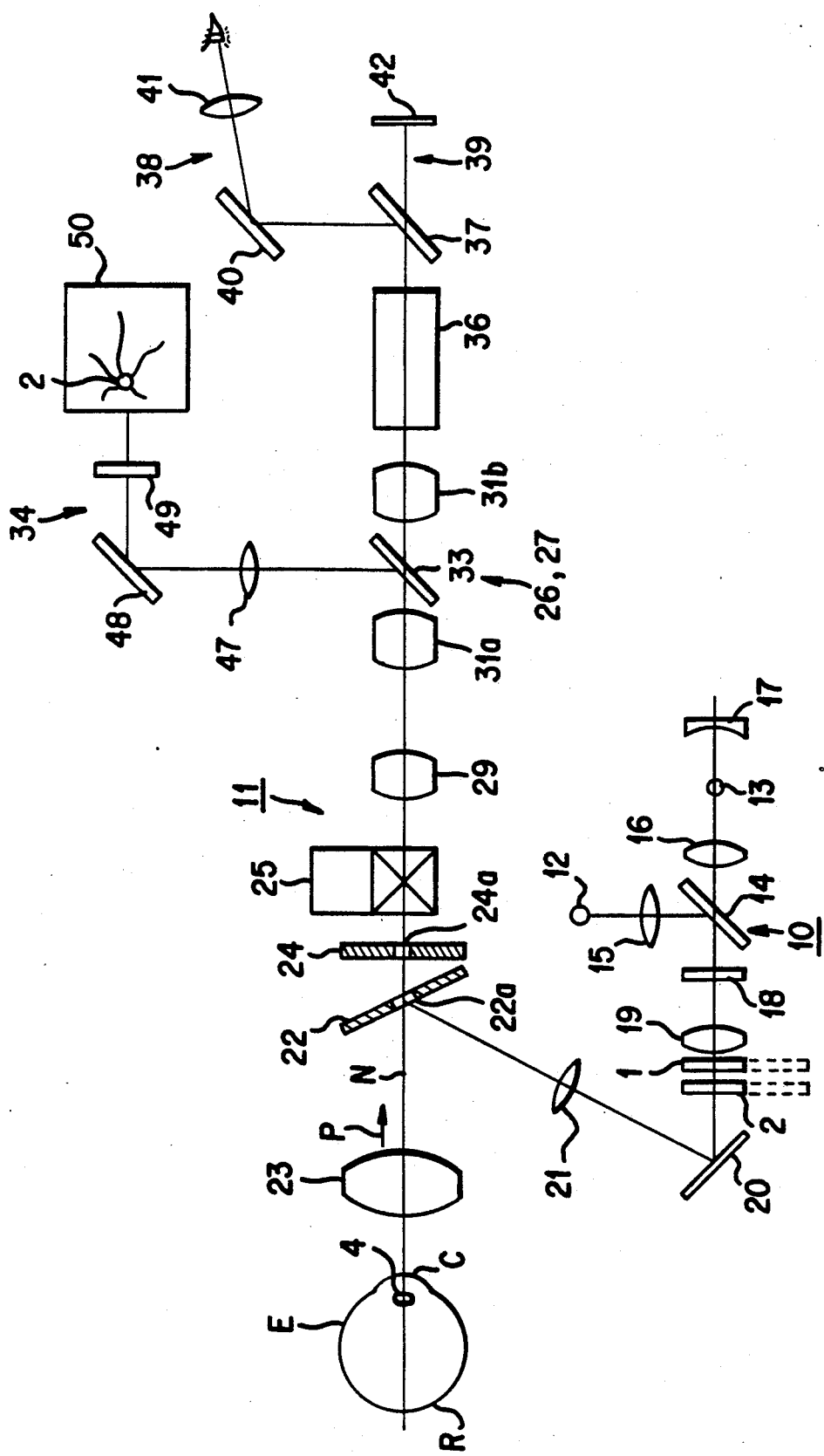
FIG. 1 is a side view of an optical system of a stereo type eye fundus camera according to the present invention.
Figure 2:
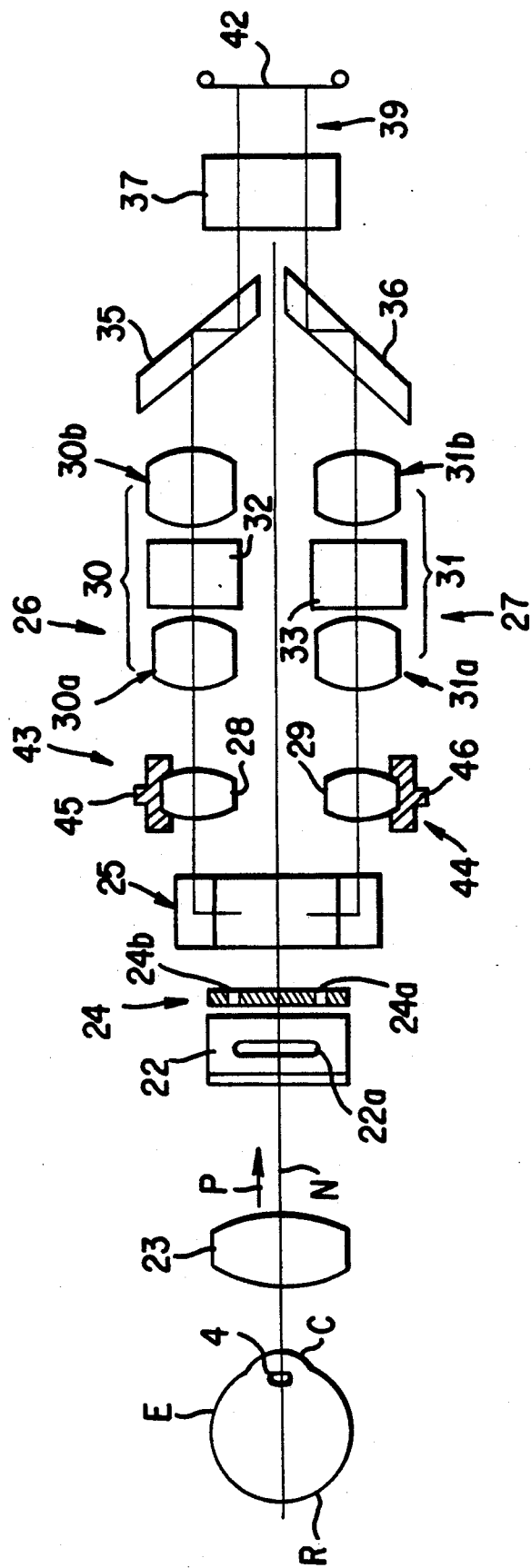
FIG. 2 is a plan view of the optical system shown in FIG. 1.

In FIGS. 1 and 2, the numeral 10 denotes an illumination optical system for the eye fundus and the numeral 11 denotes a stereo type optical systems. The eye fundus illumination optical system 10 includes a light source 12 for observation and a light source 13 for photographing. The light source 12 for observation and the light source 13 for photographing are conjugate with reference to a half mirror 14.

A condenser lens 15 is disposed between the light source 12 for observation and the half mirror 14. A condenser lens 16 is disposed between the light source 13 for photographing and the half mirror 14. A concave mirror 17 is disposed opposite the condenser lens 16 with reference to the light source 13 for photographing.

Illumination light from the light source 12 or illumination light from the light source 13 is guided to a mirror 22 via the half mirror 14, a diaphragm 18 for making ringwise ray, a relay lens 19, a filter member 1 for making a density pattern, a selection filter member 2, a reflecting mirror 20, and a relay lens 21. A mirror 22 has a hole 22a.

The illumination light is reflected by the mirror 22. The reflected light is directed to an objective lens 23. A ring-shaped illumination light transmits through a cornea C of an eye E to be tested and a crystal body 4 and illuminates an eye fundus R. The eye fundus R is illuminated by the ring-shaped illumination light.

Figure 3:
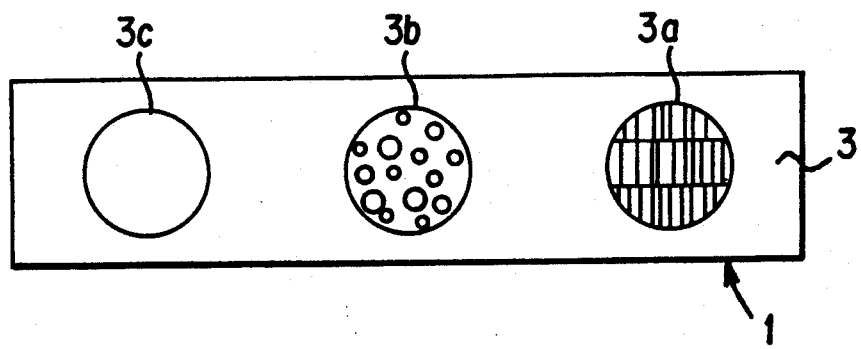
FIG. 3 is an explanatory view of a density pattern member.

The density pattern filter member 1 provided to the illumination optical system 10 includes a filter holder 3 (see FIG. 3). The filter holder 3 includes a striped pattern filter 3a, a polka dot pattern filter 3b and a colorless transparent filter 3c. Each filter 3a, 3b, 3c is selectively inserted into an optical path of the illumination optical system 10. The position of the filter member 1 is selected by using a solenoid, etc. (not shown).

This density pattern filter member 1 is slightly offset from a position conjugate with the eye fundus R with respect to the objective lens 23 in order to form a density pattern image slightly out of focus on the eye fundus R. It is preferable to form a density pattern image slightly out of focus on the eye fundus R in order to perform analysis of a three-dimensinal configuration as will be described later.

Figure 4:
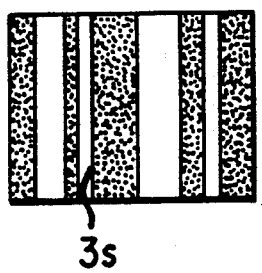
FIGS. 4 and 5 are explanatory views of density patterns.

The striped pattern filter 3a has a striped pattern (see FIG. 4). The widths of the stripes 3a and a distance between adjacent stripes 3a are random in this embodiment. However, it may be designed such that either the widths of the stripes or the distance between adjacent stripes are random. Also, when a area of searching extent is predetermined in analysis of the three-dimensional configuration, identical patterns may be repeated. More specifically, if the density pattern is random in the every area, identical patterns of density may be repeated. The area on which the indentical patterns of density may be repeated is preferably just enough to divide the papilla into ten parts in the vertical and horizontal directions.

In order to avoid a matching mistake, at least two sets of a combination of the black and white portions of the stripes of FIG. 4 are included in the area.

Figure 5:
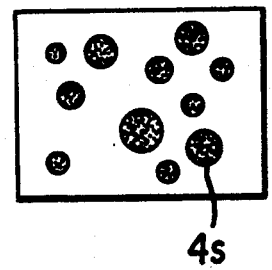

The polka dot pattern filter 3b has polka dot patterns of random sizes (see FIG. 5). However, it may be designed such that identical polka dot patterns are repeated.

Figure 6:
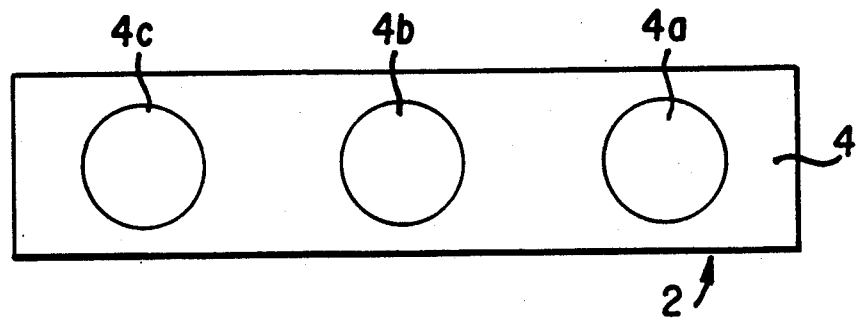
FIG. 6 is a plan view of a selection filter.

The selection filter member 2 includes a filter holder 4 (see FIG. 6). The filter holder 4 is designed to hold an infrared light transmitting filter 4a for permitting an infrared light to transmit therethrough, a visible light transmitting filter 4b for permitting a visible light to transmit therethrough, and a colorless transparent filter 4c for permitting a visible and infrared light to transmit there through. The infrared light transmitting filtere 4a, the visible light transmitting filter 4b and the colorless transparent filter 4c are selectively inserted into the optical path of the illumination optical system. The position of the selection filter member 2 is selected by using a solenoid, etc. (not shown). This selection filter member 2 can be driven independently from the density pattern filter member 1.

And when the striped pattern filter 3a or the polka dot pattern filter 3b is inserted into the optical path of the illumination optical system, a density pattern image of a striped pattern or a polka dot pattern is formed on the eye fundus R. These density pattern images can be easily distinguished from the configuration of the eye fundus R therefore, the eye fundus observation is not disturbed.

The stereo type image formation optical system 11 includes a two-aperture diaphragm 24, a poroprism 25 for erecting an image, and a pair of image formation optical systems 26 and 27 (see FIG. 2). The two-aperture diaphragm 24 has a pair of circular apertures 24a and 24b. The pair of circular apertures 24a and 24b are symmetrical in the right and left direction of the eye E with respect to the optical axis N of the objective lens 23. The two-aperture diaphragm 24 is placed in the vicinity of the mirror 22. A reflected beam P from the eye fundus R is guided to the two-aperture diaphragm 24 via the crystal body 4, the objective lens 23, and a perforation portion 22a of the perforated mirror 22. And then it becomes split beams after passing through the circular apertures 24a and 24b of the two-aperture diaphragm 24.

The poroprism 25 placed in the vicinity of the two-aperture diaphragm 24. The ring-shaped diaphragm 18 is disposed in a position conjugate with the pupil of the eye E.

The two-aperture diaphragm 24 is adapted to prevent a harmful reflected illumination light from the cornea. The harmful reflected light from the cornea can not transmit through the circular apertures 24a and 24b.

A pair of imaging optical systems 26 and 27 include focusing lenses 28 and 29, and imaging lens systems 30 and 31. The imaging lens systems 30 and 31 comprise lenses 30a, 30b, 31a and 31b, and half mirrors 32 and 33. The half mirrors 32 and 33 are disposed between the lenses 30a, 31a and 30b, 31b. The half mirrors 32 and 33 are adapted to guide a protion of the split beams to an image pickup system 34. The construction and operation of the image pickup system 34 will be described later.

The split beams transmitted through the half mirrors 32 and 33 are guided to a refleciton prisms 35 and 36 through the lenses 30b and 31b. A half mirror 37 is disposed in the vicinity of the reflection prisms 35 and 36.

An observation system 38 is branched from the half mirror 37. Similarly, a taking system 39 is branched from the half mirror 37. The observation system 38 includes a reflection mirror 40 and an ocular lens 41. Owing to the foregoing arrangement, the eye fundus image can be observed three-dimensionally. The taking system 39 is provided with a film 42. The eye fundus image is simultaneously separately formed on various parts of a sheet of film 42 with parallax. That is, for example, an eye fundus image is formed on a left-hand side of a sheet of film by one imaging optical system and another eye fundus image is formed on a right-hand side by the other imaging optical system with reference to the center of the sheet of film.

Operations will now be described.

As already described, a density pattern image is formed on the eye fundus.

Because there is a parallax between a density pattern image on a photograph obtained through one imaging optical system and another density pattern image on the photograph obtained through the other imaging optical system, a positional relation therebetween is slightly displaced. This displacement of positional relation has a certain relation with respect to the irregularities on the eye fundus. Therefore, if one density pattern image and the other density pattern image are compared with each other, the parallax can be easily measured. Accordingly, the three-dimensional configuration of the eye fundus can be easily analyzed even at portions having uniform reflection factors and at a portion, like a papilla, having a high reflection factor.

In this embodiment, the focusing lenses 28 and 29 are provided with auxiliary focusing means. The auxiliary focusing means comprise supporting members 43, 44 for movably supporting a lens, and handle portions 45, 46. The focusing lens 28 and the other focusing lens 29 can be separately and independently moved in the direction of the optical axis N of the objective lens 23.

Let us suppose here that when the apparatus was moved to achieve a well focusing so that an eye fundus image obtained by one imaging optical system would not be blurred, another eye fundus image obtained by the other imaging optical system was blurred. In this case, however, the blur of the eye fundus image obtained by the other imaging optical system can be rectified by moving the focusing lens along the optical axis N through operation of the auxiliary focusing means of the other imaging optical system. Therefore, a man can three-dimensionally observe an eye fundus image in focus.

The image pickup system 34 includes an imaging lens 47, a reflection mirror 48 and a CCD camera 49. In this embodiment, the CCD camera 49 is provided in such a manner as to correspond to each of the pair of imaging optical systems 26 and 27. If it is designed such that an image output by this CCD camera 49 is displayed on a pair of monitors 50 (only one monitor is shown), it is no more required to focus by looking through the ocular lens 41.

In the above embodiment, although the density pattern filter member 1 is disposed between the relay lens 10 and the mirror 20 of the illumination system, the present invention is not limited to this. For example, it may be designed such that an optical system for projecting a density pattern image is separately provided from the illuminatin optical system, and said optical system is provided with a density pattern filter member.

What is claimed is:

1. A stereo type eye fundus camera including an illumination optical system for illuminating the fundus of an eye to be tested, and a stereo type image formation optical system for simultaneously forming an image of the eye fundus on a sheet of film based on a reflected light from the eye fundus,
   said stereo type eye fundus camera further including a density pattern member adapted to form a density pattern image on said eye fundus.

2. A stereo type eye fundus camera according to claim 1, wherein said density pattern member is provided in said illumination optical system.

3. A stereo type eye fundus camera according to claim 1 or claim 2, wherein said density pattern member has patterns of random.

4. A stereo type eye fundus camera according to claim 1 or claim 2, wherein said density pattern member has periodically repeated patterns.

5. A stereo type eye fundus camera according to claim 1 or claim 2, wherein said stereo type image formation optical system has auxiliary focusing means.

6. A stereo type eye fundus camera according to claim 2, wherein said density pattern member is offset from a position conjugate with said eye fundus.

7. A stereo type eye fundus camera including an illumination optical system for illuminating the fundus of an eye to be tested, and a stereo type image formation optical system for simultaneously forming an image of the eye fundus on a sheet of film based on a reflected light from the eye fundus,
   said stereo type eye fundus camera being characterized in that a density pattern member is provided in said illumination optical system and said stereo type image formation optical system has image pickup means.

8. A stereo type eye fundus camera according to claim 7, wherein said density pattern member has patterns of random.

9. A stereo type eye fundus camera according to claim 7, wherein said density pattern member has periodically repeated patterns.

10. A stereo type eye fundus camera according to claim 7, wherein said stereo type image formation optical system has auxiliary focusing means.

11. A stereo type eye fundus camera according to claim 7, wherein said density pattern member is offset from a position conjugate with said eye fundus.

12. A stereo type eye fundus camera including an illumination optical system for illuminating the fundus of an eye to be tested, and a stereo type image formation optical system for simultaneously and separately forming a pair of images of the eye fundus on various component parts of a sheet of film based on a reflected light from the eye fundus,
   said stereo type eye fundus camera being characterized in that said density pattern member for forming a density pattern image on said eye fundus is provided in said illumination optical system.

* * * * *